(12) United States Patent
Lesso et al.

(10) Patent No.: US 11,653,855 B2
(45) Date of Patent: *May 23, 2023

(54) COUGH DETECTION

(71) Applicant: Cirrus Logic International Semiconductor Ltd., Edinburgh (GB)

(72) Inventors: John P. Lesso, Edinburgh (GB); Yanto Suryono, Tokyo (JP); Toru Ido, Tokyo (JP)

(73) Assignee: Cirrus Logic, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/541,904

(22) Filed: Dec. 3, 2021

(65) Prior Publication Data

US 2022/0087570 A1    Mar. 24, 2022

Related U.S. Application Data

(63) Continuation of application No. 17/097,919, filed on Nov. 13, 2020, now Pat. No. 11,219,386, which is a continuation-in-part of application No. 16/901,073, filed on Jun. 15, 2020, now Pat. No. 11,134,354.

(51) Int. Cl.
*A61B 5/08* (2006.01)
*A61B 5/083* (2006.01)
*A61B 5/00* (2006.01)

(52) U.S. Cl.
CPC .......... *A61B 5/0823* (2013.01); *A61B 5/0803* (2013.01); *A61B 5/6803* (2013.01); *A61B 5/725* (2013.01); *A61B 5/7246* (2013.01); *A61B 5/7264* (2013.01); *A61B 5/7275* (2013.01); *A61B 2562/0219* (2013.01)

(58) Field of Classification Search
CPC ................ A61B 5/0823; A61B 5/0803; A61B 5/7246; A61B 5/725; A61B 5/7264; A61B 5/7275; A61B 2562/0219; H04R 29/00
See application file for complete search history.

(56) References Cited

U.S. PATENT DOCUMENTS

| | | |
|---|---|---|
| 7,267,652 B2 | 9/2007 | Coyle et al. |
| 8,243,946 B2 | 8/2012 | Burge et al. |
| 8,891,779 B2 | 11/2014 | Michaelis |
| 9,883,278 B1 | 1/2018 | Lin et al. |
| 9,924,270 B2 | 3/2018 | Shanmugam et al. |
| 10,535,364 B1 | 1/2020 | Zhong et al. |
| 10,813,559 B2 | 10/2020 | Frank et al. |

(Continued)

FOREIGN PATENT DOCUMENTS

| | | |
|---|---|---|
| CN | 105228041 B | 8/2019 |
| CN | 110121129 A | 8/2019 |

(Continued)

OTHER PUBLICATIONS

International Search Report and Written Opinion of the International Searching Authority, International Application No. PCT/GB2021/052891, dated Feb. 18, 2022.

(Continued)

*Primary Examiner* — David L Ton
(74) *Attorney, Agent, or Firm* — Jackson Walker L.L.P.

(57) ABSTRACT

A method of cough detection in a headset, the method comprising: receiving a first signal from an external transducer of the headset; receiving a second signal from an in-ear transducer of the headset; and detecting a cough of a user of the headset based on the first and second signals.

23 Claims, 8 Drawing Sheets

(56) References Cited

U.S. PATENT DOCUMENTS

| | | |
|---|---|---|
| 11,134,354 B1 | 9/2021 | Lesso |
| 2015/0073306 A1 | 3/2015 | Abeyratne et al. |
| 2015/0256953 A1 | 9/2015 | Kwatra et al. |
| 2016/0037278 A1 | 2/2016 | Viox et al. |
| 2016/0072949 A1 | 3/2016 | Kannappan et al. |
| 2018/0132048 A1 | 5/2018 | Usher et al. |
| 2018/0152795 A1 | 5/2018 | Lee et al. |
| 2020/0015709 A1 | 1/2020 | Peltonen et al. |
| 2020/0060604 A1 | 2/2020 | Mohammadi et al. |
| 2020/0086133 A1 | 3/2020 | Wang et al. |
| 2020/0098384 A1 | 3/2020 | Nematihosseinabadi et al. |
| 2020/0245873 A1 | 8/2020 | Frank et al. |
| 2020/0297955 A1 | 9/2020 | Shouldice |
| 2020/0336846 A1 | 10/2020 | Rohde et al. |
| 2021/0027893 A1 | 1/2021 | Nematihosseinabadi et al. |
| 2021/0186350 A1 | 6/2021 | Lesso |
| 2021/0275034 A1 | 9/2021 | Frank et al. |
| 2021/0280322 A1 | 9/2021 | Frank et al. |
| 2021/0318558 A1 | 10/2021 | Tzvieli et al. |
| 2021/0392452 A1 | 12/2021 | Lesso |

FOREIGN PATENT DOCUMENTS

| | | |
|---|---|---|
| WO | 2019079909 A1 | 5/2019 |
| WO | 2021123710 A1 | 6/2021 |
| WO | 2021255415 A1 | 12/2021 |

OTHER PUBLICATIONS

International Search Report and Written Opinion of the International Searching Authority, International Application No. PCT/GB2021/051171, dated Jul. 29, 2021.

COUGH DETECTION

The present application is a continuation of U.S. Nonprovisional patent application Ser. No. 17/097,919, filed Nov. 13, 2020, which is a continuation-in-part of U.S. Nonprovisional patent application Ser. No. 16/901,073, filed Jun. 15, 2020, which is incorporated by reference herein in its entirety.

TECHNICAL FIELD

The present disclosure relates to methods and apparatus for cough detection, in particular cough detection using personal audio devices.

BACKGROUND

Headsets are used to deliver sound to one or both ears of a user, such as music or audio files or telephony signals. Modern headsets typically also comprise one or more microphones which capture sound from the surrounding environment, such as the user's voice for voice recording or telephony, or background noise signals to be used to enhance signal processing by the device and user experience.

With an ever-increasing need for portable and in-home healthcare, portable devices are increasingly being used by clinicians and other healthcare professionals for the diagnosis and monitoring of respiratory conditions. Conventional cough detectors use a microphone to monitoring cough events. Whilst these cough detectors perform well in the detection of cough events, they often incorrectly identify other noises, such as dogs barking, people shouting etc., as cough events. Thus state of the art cough detectors suffer from unacceptably high false acceptance rates (FAR) which cannot be relied upon for diagnostics and health monitoring.

SUMMARY

Embodiments of the present disclosure aim to address or at least ameliorate one or more of the above problems by providing a robust method and apparatus for cough detection which uses one or more sensors present in a personal device, such as a headset, worn by a user.

According to a first aspect of the disclosure, there is provided a method of cough detection in a headset, the method comprising: receiving a first signal from an external transducer of the headset; receiving a second signal from an in-ear transducer of the headset; and detecting a cough of a user of the headset based on the first and second signals.

In some embodiments, detecting the cough may comprise detecting a cough event in the first signal and detecting a cough event in the second signal. Detecting the cough may further comprise determining a correlation between the cough event in the first audio signal and a cough event in the second signal.

In some embodiments, detecting the cough may comprise determining a first energy in a first frequency band of the first signal, determining a second energy in a second frequency band of the first signal, and determining a third energy in a third frequency band of the second signal, wherein the first frequency band having a higher centre frequency than the second frequency band and the third frequency band. The first signal may be high pass filtered to determine the first energy. The first signal may be low pass filtered to determine the second energy. The second signal may be low pass filtered to determine the third energy.

The method may further comprise determining a change of orientation of the headset. The cough may then be detected based on the change in orientation.

In some embodiments, the in-ear transducer comprises an accelerometer. In which case, the change of orientation of the headset may be determined based on the second signal from the accelerometer.

In some embodiments, the method may comprise receiving an accelerometer signal from an accelerometer of the headset. The cough may then be detected based on the first and second signals and the accelerometer signal. The change in orientation may then determined based on the accelerometer signal.

In some embodiments, the method may further comprise high-pass filtering the second signal, in which case the cough may be detected based on the high-pass filtered second signal.

The method may further comprise determining a severity of the cough based on the second signal.

The method may further comprise, on detection of the cough, determining one or more characteristics of the cough based on the first and second signals. The one or more characteristics of the cough may be determined based on the accelerometer signal. Determining the one or more characteristics of the cough may comprise providing the first and second signals to a neural network.

In some embodiments, the method may further comprise determining a medical condition of the user based on the determined one or more characteristics of the cough. Medical conditions associated with coughs include but are not limited to laryngitis, coronavirus (e.g. COVID-19), a sore throat, croup, tonsillitis, sinusitis, asthma, allergies, gastroesophageal reflux disease (GERD), medication reactions (e.g. ACE inhibitors), exposure to irritants, pneumonia, chronic obstructive pulmonary disease (COPD) (e.g. emphysema, chronic bronchitis etc.), acute bronchitis, asthma and pertussis (whooping cough).

In some embodiments, the second transducer is a speaker of the headset. In such embodiments, the second signal may be generated based on a bias current of the speaker.

According to another aspect of the disclosure, there is provided a non-transitory storage medium having instructions thereon which, when executed by a processor, cause the processor to perform the method as described above.

According to another aspect of the disclosure, there is provided an apparatus for cough detection, comprising: a first input for receiving a first signal from an external transducer of a headset; a second input for receiving a second signal from an in-ear transducer of the headset; and one or more processors configured to: detect a cough of a user of the headset based on the first and second signals.

In some embodiments, detecting the cough may comprise detecting a cough event in the first signal and detecting a cough event in the second signal. Detecting the cough may further comprise determining a correlation between the cough event in the first audio signal and a cough event in the second signal.

In some embodiments, detecting the cough may comprise determining a first energy in a first frequency band of the first signal, determining a second energy in a second frequency band of the first signal, and determining a third energy in a third frequency band of the second signal, wherein the first frequency band having a higher centre frequency than the second frequency band and the third frequency band. The first signal may be high pass filtered to determine the first energy. The first signal may be low pass filtered to determine the second energy. The second signal may be low pass filtered to determine the third energy.

The one or more processors may be further configured to determining a change of orientation of the headset. The cough may then be detected based on the change in orientation.

In some embodiments, the in-ear transducer comprises an accelerometer. In which case, the change of orientation of the headset may be determined based on the second signal from the accelerometer.

In some embodiments, the apparatus may be further configured to receive an accelerometer signal from an accelerometer of the headset. The cough may then be detected based on the first and second signals and the accelerometer signal. The change in orientation may then determined based on the accelerometer signal.

In some embodiments, the one or more processors may be further configured to high-pass filter the second signal, in which case the cough may be detected based on the high-pass filtered second signal.

The one or more processors may be further configured to determine a severity of the cough based on the second signal.

The one or more processors may be further configured to, on detection of the cough, determine one or more characteristics of the cough based on the first and second signals. The one or more characteristics of the cough may be determined based on the accelerometer signal. Determining the one or more characteristics of the cough may comprise providing the first and second signals to a neural network.

In some embodiments, the one or more processors may be further configured to determine a medical condition of the user based on the determined one or more characteristics of the cough. Medical conditions associated with coughs include but are not limited to laryngitis, coronavirus (e.g. COVID-19), a sore throat, croup, tonsillitis, sinusitis, asthma, allergies, gastroesophageal reflux disease (GERD), medication reactions (e.g. ACE inhibitors), exposure to irritants, pneumonia, chronic obstructive pulmonary disease (COPD) (e.g. emphysema, chronic bronchitis etc.), acute bronchitis, asthma and pertussis (whooping cough).

In some embodiments, the second transducer is a speaker of the headset. In such embodiments, the second signal may be generated based on a bias current of the speaker.

According to another aspect of the disclosure, there is provided an electronic device comprising the apparatus described above. The electronic device may comprise a portable and/or battery powered device such as a mobile computing device for example a laptop or tablet computer, a games console, a remote control device, a home automation controller or a domestic appliance including a domestic temperature or lighting control system, a toy, a machine such as a robot, an audio player, a video player, or a mobile telephone for example a smartphone.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of non-limiting examples with reference to the drawings, in which.

DESCRIPTION OF EMBODIMENTS

Embodiments of the present disclosure relate to the detection and characterisation of coughing of a user of a personal audio device worn by a user and comprising one or more sensors configured to pick up sound and/or vibrations associated with coughing.

Figure 1:
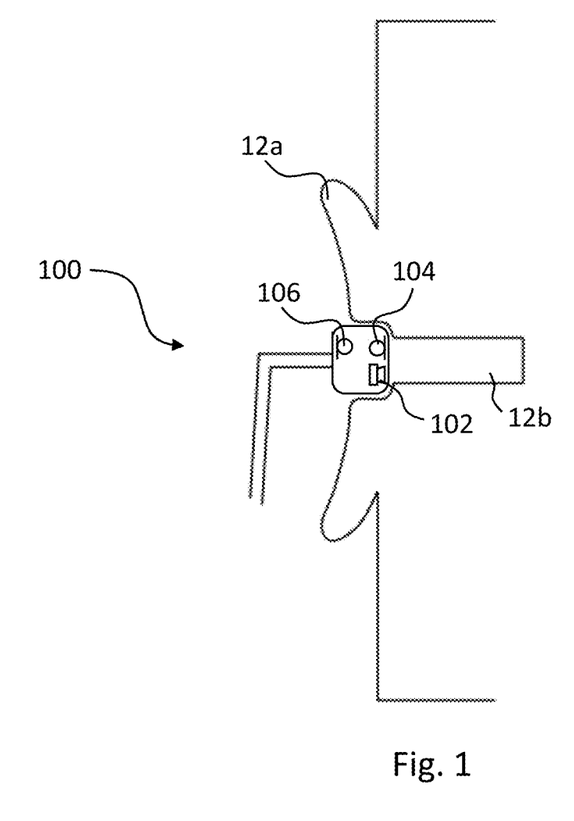
FIG. 1 is a diagram of a headphone located in ear of a user.

FIG. 1 shows a schematic diagram of a user's ear, comprising the (external) pinna or auricle 12a, and the (internal) ear canal 12b. A personal audio device comprising an intra-concha headphone 100 (or earphone) sits inside the user's concha cavity. The intra-concha headphone may fit loosely within the cavity, allowing the flow of air into and out of the user's ear canal 12b which results in partial occlusion of the ear canal of the user. Alternatively, the headphone 100 may form a tight seal with the ear canal which may result in full occlusion.

The headphone 100 comprises one or more loudspeakers 102 positioned on an internal surface of the headphone 100 and arranged to generate acoustic signals towards the user's ear and particularly the ear canal 12b. The earphone further comprises one or more microphones 104, known as error microphone(s) or internal microphone(s), positioned on an internal surface of the earphone, arranged to detect acoustic signals within the internal volume defined by the headphone 100 and the ear canal 12b. The headphone 100 may also comprise one or more microphones 106, known as reference microphone(s) or external microphone(s), positioned on an external surface of the headphone 100 and configured to detect environmental noise incident at the user's ear.

The headphone 100 may be able to perform active noise cancellation (ANC), to reduce the amount of noise experienced by the user of the headphone 100. Active noise cancellation typically operates by detecting the noise (i.e. with a microphone) and generating a signal (i.e. with the loudspeaker) that has the same amplitude as the noise signal but is opposite in phase. The generated signal thus interferes destructively with the noise and so cancels or at least lessens the noise experienced by the user. Active noise cancellation may operate on the basis of feedback signals, feedforward signals, or a combination of both, i.e. a hybrid noise cancellation arrangement. Feedforward active noise cancellation utilizes the one or more microphones 106 on an external surface of the headphone 100, operative to detect the environmental noise before it reaches the user's ear. The detected noise is processed, and the cancellation signal generated so as to inversely match the incoming noise as it arrives at the user's ear thus cancelling, or at least reducing, the noise. Feedback active noise cancellation utilizes the one or more error microphones 104, also known as feedback microphones, positioned on the internal surface of the headphone 100, operative to detect the combination of the noise and the audio playback signal generated by the one or more loudspeakers 102. This combination is used in a feedback loop, together with knowledge of the audio playback signal, to adjust the cancelling signal generated by the loudspeaker 102 and so reduce or cancel the noise. The microphones 104, 106 shown in FIG. 1 may therefore form part of an active noise cancellation system, whether it be a feedforward, feedback or hybrid system implementing both feedforward and feedback ANC.

The headphone 100 may also operate in a passthrough or transparency mode in which sound incident at the microphone 106, positioned on an external surface of the headphone, is applied to the one or more loudspeakers 102 so that a user wearing the headset 100 is able to hear their ambient acoustic environment which has otherwise been occluded due to them wearing the headset 100 and therefore has ambient awareness.

In the embodiments described herein, where feedback and/or feedforward ANC or passthrough is implemented, the microphones 104, 106 may be used both for performing feedback and/or feedforward ANC or passthrough and for providing the cough detection and identification functions as is described in detail below. In other embodiments, separate microphones may be provided for performing one or more of these functions. For example, the headphone 100 may comprise the internal microphone 104 for use in embodiments of the present disclosure (e.g. cough detection and/or identification) and an additional microphone (not shown) may be used for one or more additional ANC functions. In a further variation, the headphone 100 may utilise the speaker 102 for one or more of feedback/feedforward/hybrid ANC, passthrough, or cough detection and/or identification. For example, the speaker 102 may be used as a sensor as is known in the art. The use of a speaker as a sensor is described in U.S. Pat. No. 10,506,336, the contents of which is hereby incorporated by reference in its entirety. Where the speaker 102 is used as a sensor, the internal microphone 104 may be omitted.

In the example shown in FIG. 1, an intra-concha headphone 100 is provided as an example personal audio device. It will be appreciated, however, that embodiments of the present disclosure can be implemented on any personal audio device which is configured to be placed at, in or near the ear of a user. Examples include circum-aural headphones worn over the ear, supra-aural headphones worn on the ear, in-ear headphones inserted partially or totally into the ear canal to form a tight seal with the ear canal, or mobile handsets held close to the user's ear so as to provide audio playback (e.g. during a call). Embodiments of the present disclosure may be implemented in any type of headset that comprises at least one headphone operable to partially or fully occlude the ear. Examples include virtual reality headsets, augmented reality headsets and smart glasses to name a few.

Figure 2:
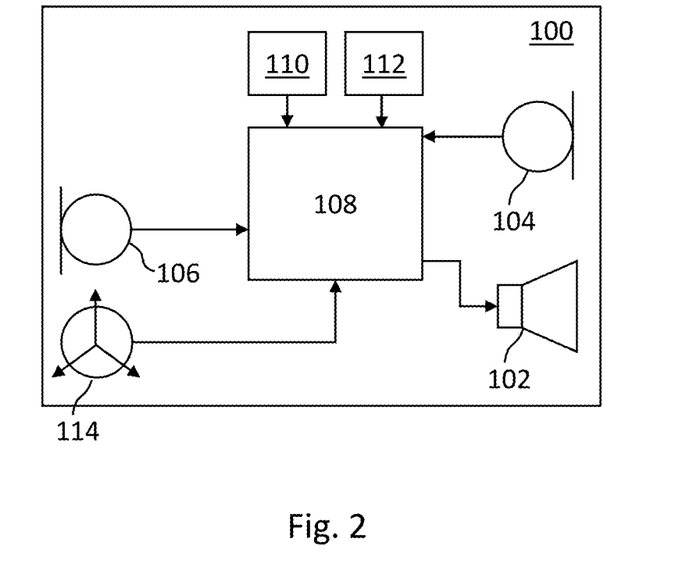
FIG. 2 is a schematic diagram of the headphone of FIG. 1.

FIG. 2 is a system schematic of the headphone 100. The headphone 100 may form part of a headset comprising another headphone (not shown) configured in substantially the same manner as the headphone 100. The pair of headphones (the headphone 100 and the other headphone which is not shown) may form a stereo headset.

A signal processor 108 of the headphone 100 is configured to receive microphone signals from the microphones 104, 106 and output audio signals to the loudspeaker 102. When the headphone 100 is positioned at, near or within the ear canal, the microphone 104 is occluded to some extent from the external ambient acoustic environment. The headphone 100 may be configured for a user to listen to music or audio, to make telephone calls, to deliver voice commands to a voice recognition system, and/or other such audio processing functions. The processor 108 may be configured to implement active noise cancellation (feedback and/or feedforward) and/or passthrough/transparency modes using the microphones 104, 106 and the one or more transducers 102.

The headphone 100 further comprises a memory 110, which may in practice be provided as a single component or as multiple components. The memory 110 is provided for storing data and/or program instructions. The headphone 100 further may further comprise a transceiver 112, which is provided for allowing the headphone 100 to communicate (wired or wirelessly) with external devices, such as another headphone, and/or a host device, such as a mobile device (e.g. smartphone) for example, to which the headphone 100 is coupled. Such communications between the headphone 100 and external device(s) may comprise wired communications where suitable wires are provided between left and right sides of a headset, either directly such as within an overhead band, or via an intermediate device such as a mobile device and/or wireless communications. The headphone may be powered by a battery and may comprise other sensors (not shown).

The headphone 100 may further comprise an inertial measurement unit (IMU) 114 sensor, such as an accelerometer or gyroscope, which may be configured to output inertial measurements to the processor 108. The IMU 114 may form part of the headphone 100. Alternatively, the IMU 114 may be a separate module in communication with the headphone 100, for example, via the transceiver 112. In some embodiments, for example where the headphone 100 is implemented as a headset worn on a user's head, the IMU 114 may be positioned away from the ear of the user when worn, for example on the nose bridge of a pair of smart glasses. The IMU 114 may be used to generate one or more signals representative of motion of the headphone 100 which may be used as a proxy for motion of the head of a user upon which the headphone 100 is being worn. Examples of motion include movement (forward, back, left, right, up, down) as well as tilt in any direction. A change in movement or tilt may also be derived from signals received from the IMU 114. Since coughing leads to motion of the head and body, the IMU 114 may be used to determine one or more characteristics of a cough based on characteristics of the detected motion at the IMU 114.

Embodiments of the present disclosure may utilise signals derived from the internal microphone 104, the speaker 102, the IMU 114 and/or the external microphone 106 to detect that a user or wearer of the headphone 100 has coughed. Embodiments of the present disclosure may also utilise one or more of these signals to determine one or more characteristics of the cough.

Figure 3:
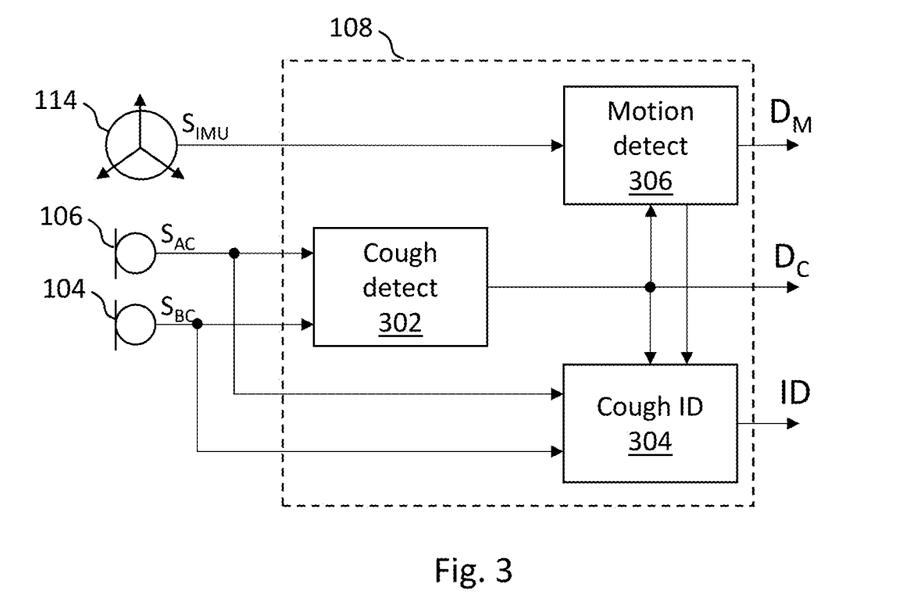
FIG. 3 is a schematic diagram illustrating a processor of the headphone of FIGS. 1 and 2 in more detail.

FIG. 3 is a block diagram showing the signal processor 108 according to some embodiments of the disclosure. For clarity, the memory 110 and transceiver 114 are not shown.

The processor 108 may comprises a cough detect module 302. The processor 108 may comprise a cough identification (ID) module 304. The processor 108 may comprise a motion detect module 306.

The cough detect module 302 may receive first and second signals from respective external and internal microphones 106, 104 and output a cough indication $D_C$. The first signal is referred to herein as $S_{AC}$. The second signal is referred to herein as $S_{BC}$. The cough detect module 302 may be configured to detect a cough event associated with a cough of the user of the headphone. Whilst not shown in FIG. 3, in some embodiments, the cough detect module 302 may also receive an IMU signal, $S_{IMU}$, from the IMU 114.

The motion detect module 306 may receive the IMU signal, $S_{IMU}$, from the IMU 114 and optionally the cough indication $D_C$ from the cough detection module 302 and output a motion indication $D_M$. The motion detect module 306 may also receive the cough indication $D_C$ from the cough detect module 302. The motion detect module 306 may process the IMU signal from the IMU 114 and determine a motion of the headphone 100 and therefore the user, for example during the cough.

The cough ID module 304 may receiving the first and second signals $S_{AC}$, $S_{BC}$ from respective external and internal microphones 106, 104 and optionally the cough indication $D_C$, and output a cough ID. The cough ID module 304 may also receive the motion indication $D_M$ from the motion detect module 306. Whilst not shown in FIG. 3, in some embodiments, the cough ID module 304 may also receive an IMU signal, $S_{IMU}$, from the IMU 114.

The first signal $S_{AC}$ is representative of the acoustic path between the user's mouth and the ear of the user. As such, when a user of the headphone 100 coughs, the sound of the cough originating from the user's mouth will be picked up in the first signal $S_{AC}$. A benefit of detecting coughs using $S_{AC}$ is the reasonably high power of the cough in the acoustically conducted signal. A drawback of detecting a cough originating from a user of the headphone is that the external microphone 106 is subject to noise due to audio artefacts not associated with the user, such as the noise of other people (talking, coughing etc.), the dogs barking, the slamming of doors to name a few.

Due to the internal microphone 104's position internal to the headphone 102 proximate the user's head, the second signal $S_{BC}$ is representative of bone conducted sound originating from the throat and chest of the user. For example, when a user of the headset 100 coughs, the first signal $S_{BC}$ derived from the internal microphone 104 is representative of the bone conducted sound associated with the user coughing. Due to the internal microphone 104's position on an internal surface of the headphone 100 and the at least partial occlusion of the ear canal by the headphone 100, external sound received at the internal microphone 104 is substantially reduced when compared to the external microphone 106. As such, the bone conducted signal $S_{BC}$ is less susceptible to external noise.

Figure 4:
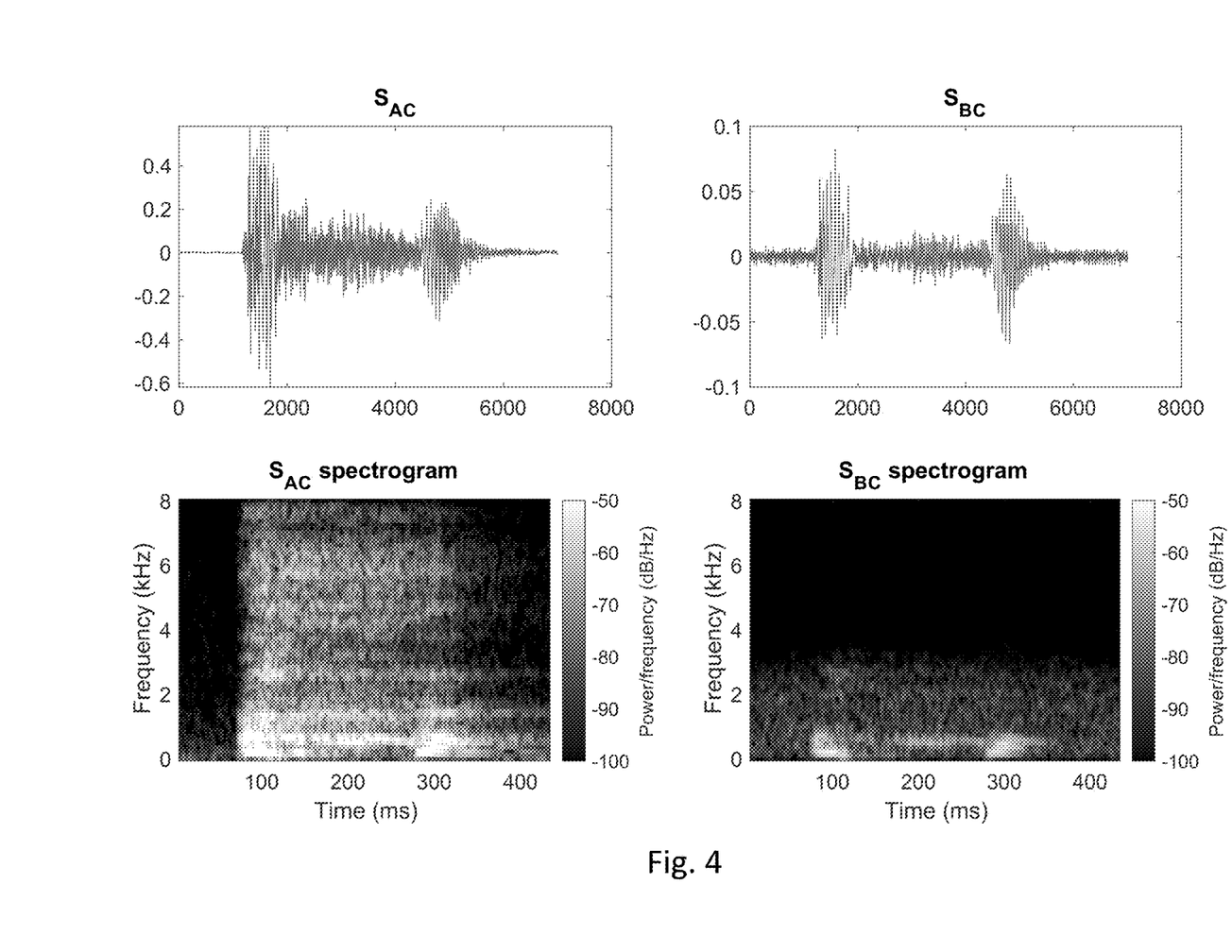
FIG. 4 is a graphical illustration of a sound recorded using the external and internal microphones of the headphone shown in FIG. 1 while a user coughs.

FIG. 4 graphically illustrates a soundwave and spectrogram for each of $S_{AC}$ (left) and $S_{BC}$ (right) representative of a typical cough. It can be seen that characteristics of the cough picked up in the bone conducted signal $S_{BC}$ can be used to reduce the false acceptance rate (FAR) associated with the acoustically conducted signal $S_{AC}$ whilst also maintaining a low false rejection rate (FRR). Since the bone conducted signal $S_{BC}$ is less susceptible to environmental noise, by utilising the second signal, $S_{BC}$, from the internal microphone 104 in addition to the first signal, $S_{AC}$, from the external microphone 106, the cough detector 302 may detect a cough of the user with a lower false acceptance rate (FAR) when compared to relying on a single external.

Figure 5:
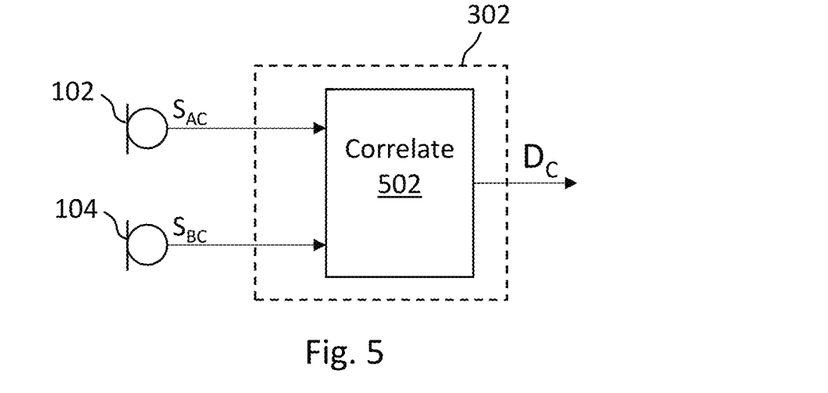
FIG. 5 is a schematic diagram of a cough detect module.

FIG. 5 is a schematic diagram of the cough detector 302 according to an embodiment of the disclosure. The cough detector 302 comprises a correlation detector 502 configured to determine a correlation between the first and second signals $S_{AC}$ and $S_{BC}$. If the correlation between the first and second signals exceeds a threshold, the correlation detector 502 may output an indication, $D_C$, that the user has coughed. The cough indication, $D_C$, may be a binary flag indicating that a cough has occurred. Alternatively the cough indication, $D_C$, may be a probability that the user has coughed. For example, the probability may be determined based on the correlation between the first and second signals $S_{AC}$ and $S_{BC}$, the greater the correlation between the two signals, the greater the probability of the user having coughed.

In embodiments described herein, the bone conduction signal $S_{BC}$ is derived from the internal microphone 104. In alternative embodiments, this signal may be generated by the IMU 114 or another IMU (not shown) positioned on or in the headphone 102. Additionally, or alternatively, the cough detect module 302 may receive the IMU signal $S_{IMU}$ from the IMU 114. The cough detector 302 may detect a cough of the user based on $S_{AC}$ and $S_{BC}$, or $S_{AC}$ and $S_{IMU}$, or $S_{BC}$, $S_{AC}$ and $S_{IMU}$. For example, where the cough detector 302 receives $S_{BC}$, $S_{AC}$ and $S_{IMU}$, the correlation detector 502 may determine a correlation between all three signals, and output the cough indication, $D_C$, based on the correlation between all three signals.

The above method enables a distinction to be made between audible events initiated by the user (e.g. the speech or cough of the user of the headphone 100 vs the speech or cough of third parties). The inventors have realised that the acoustic and bone conducted signals, $S_{AC}$ and $S_{BC}$, can also be used to distinguish between speech of the user of the headphone 100, a cough of the user of the headphone 100 and silence.

Normal speech may be categorised into voiced speech and unvoiced speech. Speech is composed of phonemes, which are produced by the vocal cords and the vocal tract (which includes the mouth and the lips). Voiced signals are produced when the vocal cords vibrate during the pronunciation of a phoneme. Unvoiced signals, by contrast, do not entail the use of the vocal cords. For example, the only difference between the phonemes /s/ and /z/ or /f/ and /v/ is the vibration of the vocal cords. Voiced signals tend to be louder like the vowels /a/, /e/, /i/, /u/, /o/. Unvoiced signals, on the other hand, tend to be more abrupt like the stop consonants /p/, /t/, /k/.

Thus, voiced speech tends to have its energy concentrated at lower frequencies and this is where the first and second signals, $S_{AC}$ and $S_{BC}$, correlate well since lower frequencies conducts better than high frequencies through bone. In contrast, unvoiced speech tends to have its energy concentrated at higher frequencies. As such, unvoiced speech tends to be present at much lower energy in bone conducted sound, i.e. the second signal $S_{BC}$. In contrast to voiced and unvoiced speech, coughing is unvoiced, but has a unique characteristic in that its energy is distributed through both low and high frequencies.

Figure 6:
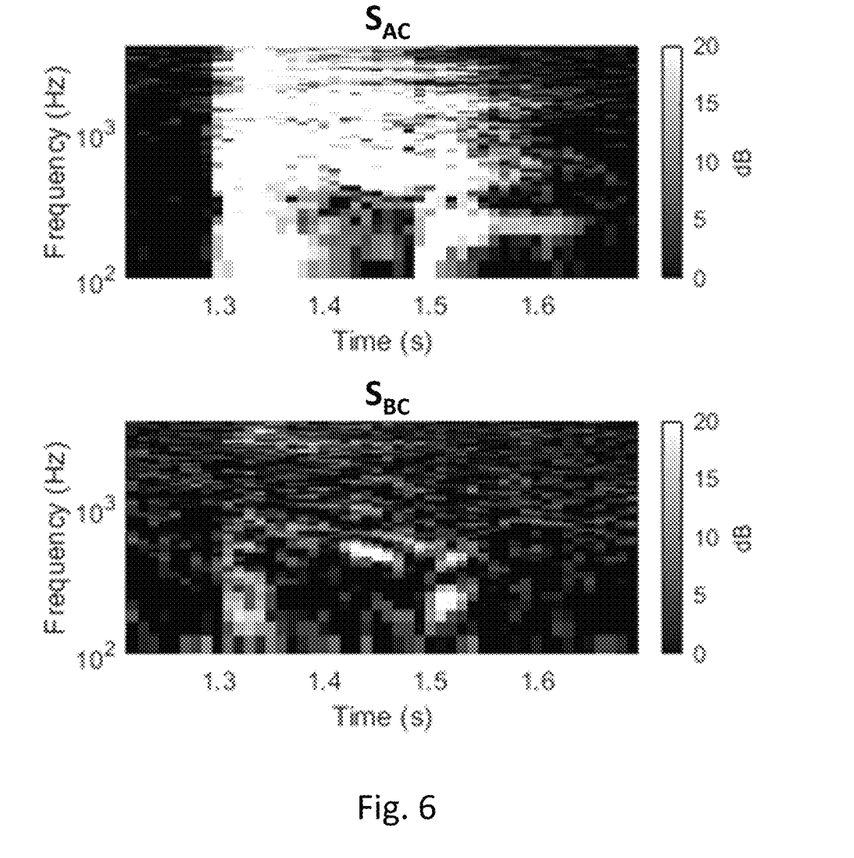
FIG. 6 is a graphical illustration of a spectrogram of sound recorded using the external and internal microphones of the headphone shown in FIG. 1 while a user coughs.

FIG. 6 shows the spectrograms for the acoustic and bone conducted first and second signals $S_{AC}$ and $S_{BC}$ during a cough of the user. It can be seen that the energy in the acoustically conducted signal $S_{AC}$ representing the cough is distributed across the frequency spectrum (i.e. at both high and low frequencies). The bone conducted signal $S_{BC}$ representing the cough is concentrated at lower frequencies.

Figure 7:
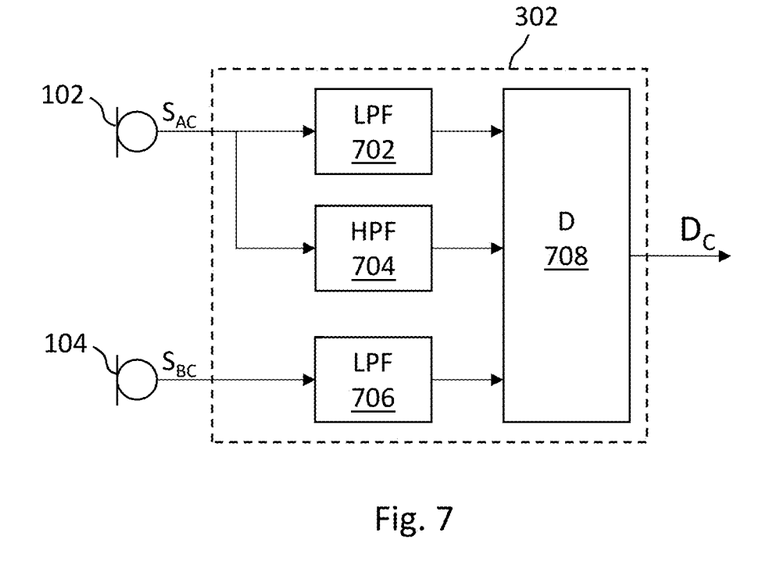
FIG. 7 is a schematic diagram of a cough detect module.

FIG. 7 is a schematic diagram of the cough detector 302 according to another embodiments of the present disclosure which utilises the characteristics of a user's cough to distinguish the user's cough on the one hand to voiced and unvoiced speech of either the user or third parties on the other hand. The cough detector 302 comprises a first low pass filter (LPF) 702, a high pass filter (HPF) 704, a second LPF 706 and a decision module 708. The first LPF 702 and the HPF 704 receive the first signal $S_{AC}$ from the first microphone 102. The first LPF 702 outputs a low pass filtered first signal to the decision module 708. The HPF 704 outputs a high pass filtered first signal to the decision module 708. The second LPF 706 receives the second signal $S_{AC}$ from the second microphone 102 and outputs a low pass filtered second signal to the decision module.

Based on the low pass filtered first signal, the high pass filtered first signal and the low pass filtered second signal, the decision module 708 determines whether a cough event has taken place, i.e. whether the user of headphone 100 has coughed. Below is a table indicating the expected energy levels in the high and low pass filtered first signal (high- and low-pass filtered $S_{AC}$) and the low pass filtered second signal (low pass filtered version of $S_{BC}$). In the table, "L" denotes low energy and "H" denotes high energy.

|  | Silence | BC Noise (User) | Voiced (Other) | Voiced (Self) | Unvoiced (Anyone) | BC Noise (Anyone) (unvoiced) | Cough (Other) | Cough (User) |
|---|---|---|---|---|---|---|---|---|
| Higher band energy ($S_{AC}$) | L | L | L | L | H | H | H | H |
| Lower band energy ($S_{AC}$) | L | L | H | H | L | L | H | H |
| Lower band energy ($S_{BC}$) | L | H | L | H | L | H | L | H |

It can be seen from the above that only coughing exhibits high energy content at both high and low frequencies and therefore high energy in all of the high- and low-pass filtered first signal and the low-pass filtered second signal.

The decision module 708 may thus determine whether an energy or envelope of each of the signals output from the first LPF 702, the HPF 704 and the second LPF 706 exceeds a respective threshold. The threshold may be the same for all signals or may be specific to each signal. If the energy in each of these filtered signals exceeds the respective thresholds, the decision module 78 may then output an indication, $D_C$, that the user has coughed. The cough indication, $D_C$, may be a binary flag indicating that a cough has occurred. Alternatively the cough indication, $D_C$, may be a probability that the user has coughed. Where a probability is output from the decision module 708, thresholding may not take place. For example, the probability that a cough has occurred may be proportional to the energy level in each of the signals output from the first LPF 702, the HPF 704 and the second LPF 706.

Figure 8:
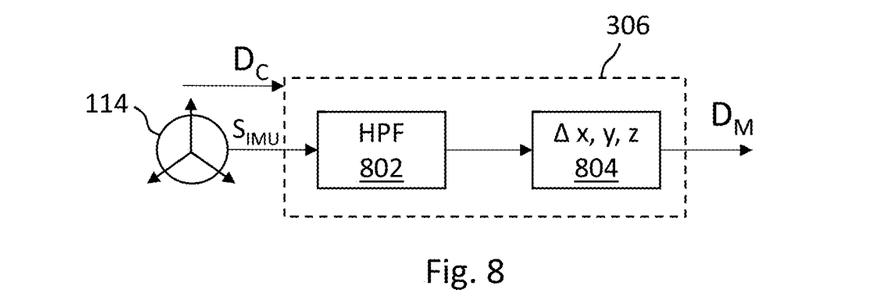
FIG. 8 is a schematic diagram of a motion detect module.

FIG. 8 is a schematic diagram of the motion detect module 306 according to an embodiment of the disclosure. The inventors have identified that coughing is often accompanied by involuntary movement of the body and head. The inventors have also realised that different movements are associated with different types of coughs. As such, the IMU 114 of the headphone 100 may be used for several purposes. Firstly, the IMU 114 can be used to detect motion of the user, for example due to a cough. Secondly, the IMU 114 may be used to determine the type of cough which has taken place, for example based on the direction of movement and severity (velocity and acceleration) of the movement.

The motion detect module 306 may optionally receive the cough detect signal $D_C$ from the cough detect module 302. The motion detect module 306 or the output from the motion detect module 306 may be gated based on the cough detect signal DC. For example, the motion detect module 306 may only operate when it is determined that the user has coughed or has likely coughed. For example, the motion detect module 306 may only output a motion change signal $D_M$ when it is determined that the user has coughed or has likely coughed.

The motion detect module 306 may comprise a high pass filter (HPF) 802 configured to receive and high pass filters the IMU signal $S_{IMU}$ to remove static orientation information from the IMU signal. The signal output from the HPF 802 is representative of a change of orientation of the IMU 114 and thus the headphone 100. The output from the HPF 802 is provided to motion module 804 configured to generate and output a signal representative of a change of orientation of the IMU 114 in one or more axes. For example, if the IMU 114 is a single axis IMU 114 (e.g. x), the output signal may be representative of a change of orientation in a single direction. For example, if the IMU 114 is a two-axis IMU 114 (e.g. x & y), the output signal may be representative of a change of orientation in two orthogonal directions. For example, if the IMU 114 is a three-axis IMU 114 (e.g. x, y, z), the output signal may be representative of a change of orientation in three orthogonal directions. As mentioned above with reference to FIG. 3, this motion signal $D_M$ is output from the motion module 804 and provided to the cough ID module 304.

Referring again to FIG. 3, the cough ID module 304 may receive the first and second (acoustic and bone conducted signals) as well as the motion change signal $D_M$ and the cough detect $D_C$. In some embodiments the cough detect signal $D_C$ may be used to gate the cough ID module 304, the cough ID module 304 only performing analysis on the first and second signals $S_{AC}$ and $S_{BC}$ on receive of a positive cough detect signal $D_C$. Using one or more of these signals may be configured to output a cough ID signal indicating a cough type as well as other information regarding a user's cough such as cough duration and severity. Types of cough include but are not limited to wet cough (or productive), dry cough, paroxysmal cough and barking (croup) cough. Types of cough may be specifically related to a condition, disorder or disease. For example, dry coughs may relate to laryngitis, coronavirus (e.g. COVID-19), a sore throat, croup, tonsillitis, sinusitis, asthma, allergies, gastroesophageal reflux disease (GERD), medication reactions (e.g. ACE inhibitors), exposure to irritants. For example, dry coughs may be associated with coronavirus (e.g. common cold or COVID-19), pneumonia, chronic obstructive pulmonary disease (COPD) (e.g. emphysema, chronic bronchitis etc.), acute bronchitis and asthma. Paroxysmal coughing is a cough with intermittent attacks of violent uncontrollable coughing, which may be caused by pertussis (whooping cough). Barking coughs have a characteristic "barking" sound due to swelling in and around the larynx. It will be appreciated that each of these cough types have different sounds and different physical actions associated with them which, when recorded by a microphone and inertial measurement unit, can be detected.

Thus, the cough ID module may be configured, to analyse the first signal $S_{AC}$, the second signal $S_{BC}$ and the motion signal $D_M$ to determine a characteristic and/or type of cough and a suspected condition, disease and/or disorder associated with the determined cough type. For example, a wet cough may be detectable in the first signal $S_{AC}$ due to their signature sound associated with pushing mucus out of the respiratory system. For example, a dry rasping or barking cough may be particularly detectable in the second signal $S_{BC}$ due to the vibration of the vocal cords associated with such coughs. The cough ID module 304 may combine the analysis of the first and second signals with motion information from the motion change signal $D_M$ received from the motion detect module 306 to determine what is likely to be causing the cough. For example, dry coughs due to pneumonia can cause a sufferer to lean forward violently while coughing. This movement may be present in the motion change signal $D_M$. When combined with the dry cough signature in the first and/or second signals $S_{AC}$, $S_{BC}$, the cough ID module 304 may determine that the user is suffering from a dry cough which may be caused by pneumonia.

In some embodiments, the cough ID module may use machine learning based on one or more of the first signal $S_{AC}$, the second signal $S_{BC}$, the motion signal $D_M$ and the IMU signal $S_{IMU}$ to determine a cough type. For example, a neural network may be trained on examples of these signals comprising different types of coughs. The trained neural network may then be provided one or more of the first signal $S_{AC}$, the second signal $S_{BC}$, the motion signal $D_M$ and the IMU signal $S_{IMU}$ and output a determination of one or more of a cough type, a disease, a condition and a disorder.

However the cough ID is generated, the cough ID may be output from the cough ID module 304 for further processing.

Figure 9:
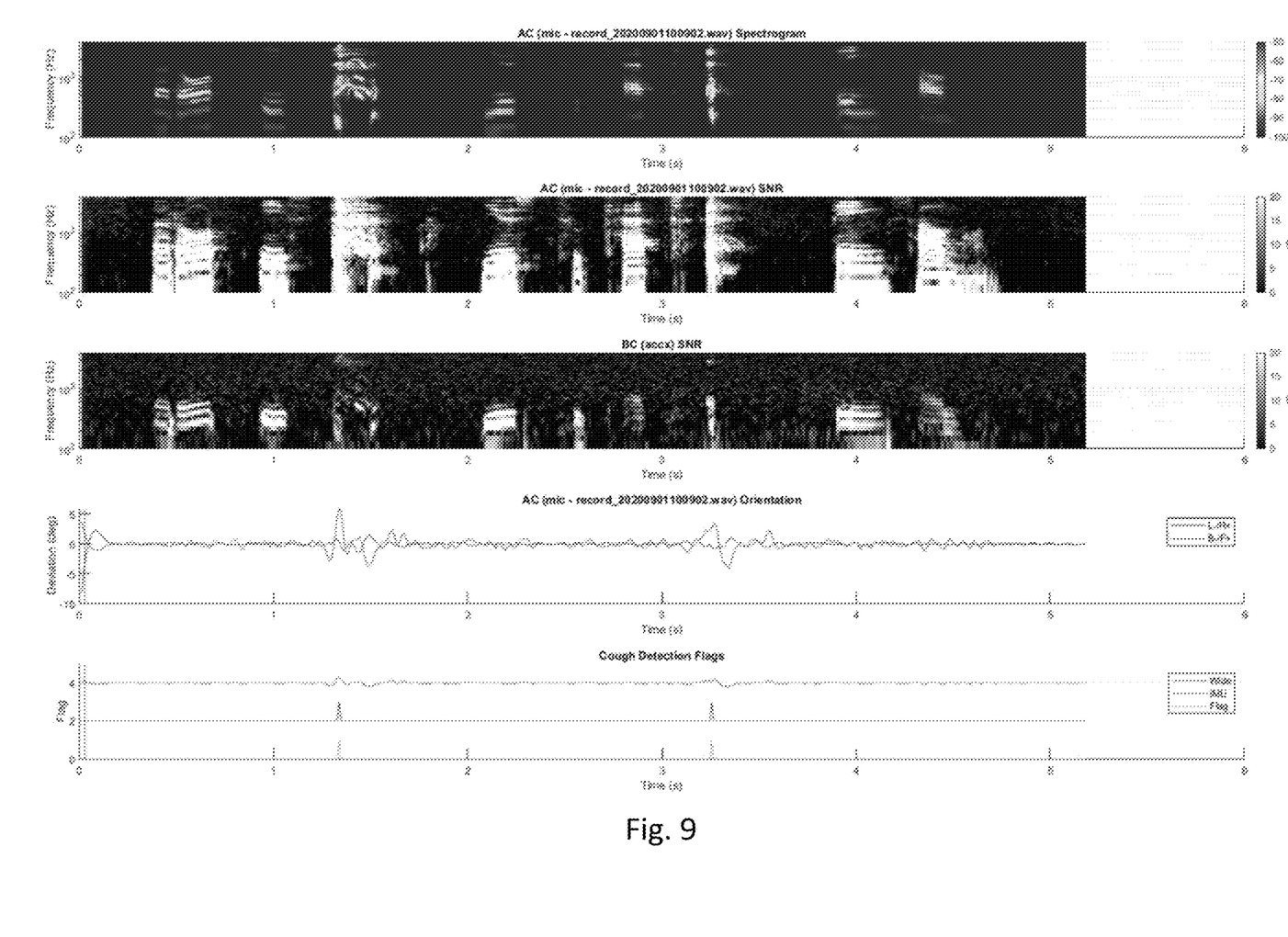
FIG. 9 is a graphical illustration of a sound recorded using the external and internal microphones and the inertial measurement unit (IMU) of the headphone shown in FIG. 1 while a user coughs.

FIG. 9 is a graphical illustration of (from top to bottom) the first and second signals $S_{AC}$ and $S_{BC}$, the motion signal $D_M$, and the cough detect signal $D_C$ according to an embodiment of the disclosure. It can be seen from this illustration that the motion of the IMU 114 coincides with the cough events between 1 and 2 seconds and between 3 and 4 seconds. It can also be seen from the cough detect signal $D_C$ that a cough is detected based on these first and second signals $S_{AC}$ and $S_{BC}$.

As mentioned above, in some embodiments, the second signal $S_{BC}$ may be generated using the speaker 102 used as a sensor as is known in the art. This may be advantageous where the signal from the internal microphone 104 has been pre-processed to remove low frequency noise (such as wind noise).

Figure 10:
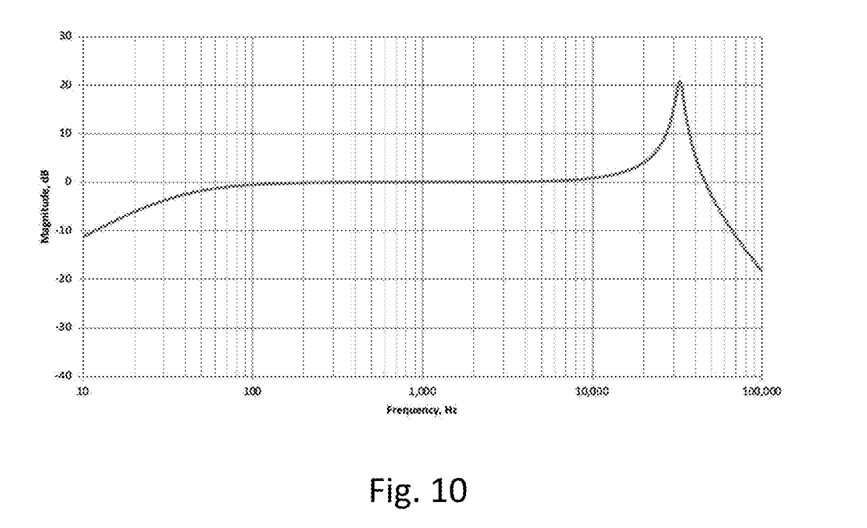
FIG. 10 is a graph illustrating the frequency response of a microphone.

FIG. 10 graphically illustrates the microphone frequency response characteristic for microphones such as the internal microphone 104 which is typically incorporated into headphones such as the headphone 100. Such microphones are designed with low frequency roll off to reduce sensitivity to wind noise. Additionally, package noise of such microphones increases significantly below around 1 kHz. The speaker 102 on the other hand does not suffer to the same extent. As such, the speaker 102 may be used in place of (or in addition to) the internal microphone 104 to detect the bone conducted signal $S_{BC}$.

Figure 11:
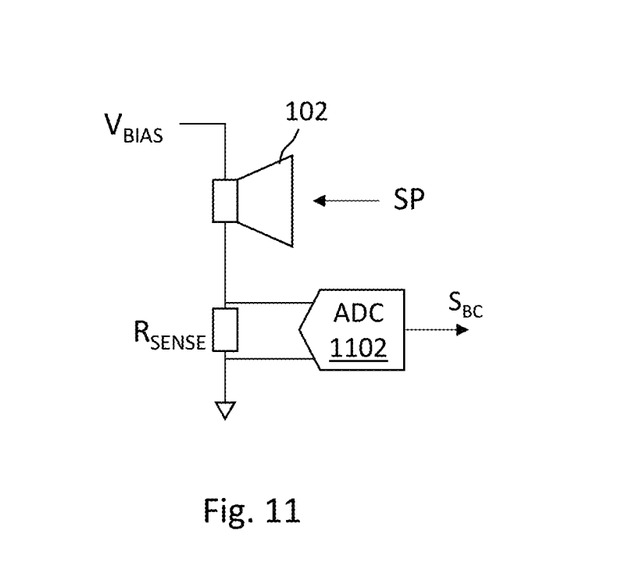
FIG. 11 is a circuit diagram for detecting a change in sound pressure at a speaker.

FIG. 11 is an exemplary circuit for use in detecting sound pressure (SP) incident at the microphone 102, in the form of a current monitor configuration. A bias voltage is applied across input terminals of the speaker 102. A resistor $R_{SENSE}$ is positioned between an input terminal and ground. A voltage across the resistor is then monitored, for example, using an analogue-to-digital converter (ADC) 1102 configured to convert the analogue voltage drop into a digital representation. A change in sound pressure at the speaker 102 results in a change in impedance of the speaker 102 which in turn results in a change in voltage drop across the resistor $R_{SENSE}$. As mentioned above, the use of a speaker as a sensor is described in U.S. Pat. No. 10,506,336, the contents of which is hereby incorporated by reference in its entirety, and so this concept will not be described in further detail here.

Figure 12:
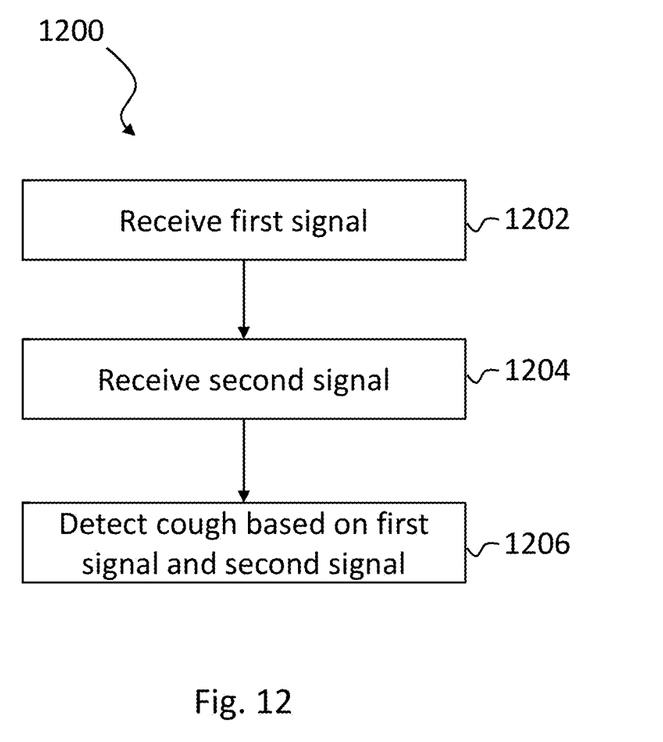
FIG. 12 is a block diagram of a process according to embodiments of the disclosure.

FIG. 12 is a block diagram of a process 1200 according to various embodiments of the present disclosure which may be performed by the signal processor 108.

At step 1202 the signal processor 108 may receive a first signal, for example, a first audio signal from the external microphone 106 of the headphone 100.

At step 1204 the signal processor 108 may receive a second signal, for example, an audio signal from the internal microphone 104 of the headphone 100, or the IMU signal from the IMU 114 or a signal derived from the speaker 102 (such as that described with reference to FIG. 11).

At step 1206, the signal processor 108 may then detect a cough of the user based on the received first and second signals.

The skilled person will recognise that some aspects of the above-described apparatus and methods may be embodied as processor control code, for example on a non-volatile carrier medium such as a disk, CD- or DVD-ROM, programmed memory such as read only memory (Firmware), or on a data carrier such as an optical or electrical signal carrier. For many applications embodiments of the invention will be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog TM or VHDL (Very high-speed integrated circuit Hardware Description Language). As the skilled person will appreciate, the code may be distributed between a plurality of coupled components in communication with one another. Where appropriate, the embodiments may also be implemented using code running on a field-(re)programmable analogue array or similar device in order to configure analogue hardware.

Note that as used herein the term module shall be used to refer to a functional unit or block which may be implemented at least partly by dedicated hardware components such as custom defined circuitry and/or at least partly be implemented by one or more software processors or appropriate code running on a suitable general purpose processor or the like. A module may itself comprise other modules or functional units. A module may be provided by multiple components or sub-modules which need not be co-located and could be provided on different integrated circuits and/or running on different processors.

Embodiments may be implemented in a host device, especially a portable and/or battery powered host device such as a mobile computing device for example a laptop or tablet computer, a games console, a remote control device, a home automation controller or a domestic appliance including a domestic temperature or lighting control system, a toy, a machine such as a robot, an audio player, a video player, or a mobile telephone for example a smartphone.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

The invention claimed is:

1. An apparatus for cough detection, comprising:
   a first input for receiving a first signal from a first transducer of a personal audio device;
   a second input for receiving a second signal from a second transducer of the personal audio device; and
   one or more processors configured to:
      detect a cough of a user of the personal audio device based on the first and second signals, wherein detecting the cough comprises:
         detecting a cough event in the first signal;
         detecting a cough event in the second signal.

2. The apparatus of claim 1, wherein the first transducer is an external transducer and the second transducer is an in-ear transducer.

3. The apparatus of claim 1, wherein detecting the cough comprises:
   determining a correlation between the cough event in the first audio signal and a cough event in the second signal.

4. The apparatus of claim 1, wherein detecting the cough comprises:
   determining a first energy in a first frequency band of the first signal;
   determining a second energy in a second frequency band of the first signal; and
   determining a third energy in a third frequency band of the second signal, wherein the first frequency band has a higher centre frequency than the second frequency band and the third frequency band.

5. The apparatus of claim 4, wherein:
   determining the first energy comprises high pass filtering the first signal;
   determining the second energy comprises low pass filtering the first signal; and
   determining the third energy comprises low pass filtering the second signal.

6. The apparatus of claim 5, further comprising:
   determining a change of orientation of the personal audio device; and
   detecting the cough based on the change in orientation.

7. The apparatus of claim 6, wherein the second transducer comprises an accelerometer, and wherein the change of orientation of the personal audio device is determined based on the second signal from the accelerometer.

8. The apparatus of claim 6, wherein the personal audio device further comprises an accelerometer configured to generate an accelerometer signal, the one or more processors configured to detect the cough based on the first and second signals and the accelerometer signal.

9. The apparatus of claim 8, wherein the change in orientation is determined based on the accelerometer signal.

10. The apparatus of claim 6, further comprising:
high-pass filtering the second signal, wherein the cough is detected based on the high-pass filtered second signal.

11. The apparatus of claim 6, further comprising:
determining a severity of the cough based on the second signal.

12. The apparatus of claim 1, wherein the one or more processors are further configured to:
on detection of the cough, determine one or more characteristics of the cough based on the first and second signals.

13. The apparatus of claim 12, wherein the personal audio device further comprises an accelerometer configured to generate an accelerometer signal, the one or more processors are further configured to:
determine the one or more characteristics of the cough based on the accelerometer signal.

14. The apparatus of claim 12, wherein determining the one or more characteristics of the cough comprises:
providing the first and second signals to a neural network.

15. The apparatus of claim 12, wherein the one or more processors are further configured to:
determine a medical condition of the user based on the determined one or more characteristics of the cough.

16. The apparatus of claim 15, wherein the medical condition comprises asthma or croup or chronic obstructive pulmonary disease (COPD) or pneumonia or coronavirus or influenza.

17. The apparatus of claim 1, wherein the second transducer is a speaker of the personal audio device.

18. The apparatus of claim 17, wherein the second signal is generated based on a bias current of the speaker.

19. A method of cough detection in a personal audio device, the method comprising:
receiving a first signal from a first transducer of the personal audio device;
receiving a second signal from a second transducer of the personal audio device; and
detecting a cough of a user of the personal audio device based on the first and second signals, wherein detecting the cough comprises:
detecting a cough event in the first signal;
detecting a cough event in the second signal.

20. A non-transitory storage medium having instructions thereon which, when executed by a processor, cause the processor to perform a method
receiving a first signal from a first transducer of the personal audio device;
receiving a second signal from a second transducer of the personal audio device; and
detecting a cough of a user of the personal audio device based on the first and second signals, wherein detecting the cough comprises:
detecting a cough event in the first signal;
detecting a cough event in the second signal.

21. An electronic device comprising the apparatus of claim 1.

22. An apparatus for cough detection, comprising:
a first input for receiving a first signal from a first transducer of a personal audio device;
a second input for receiving a second signal from a second transducer of the personal audio device; and
one or more processors configured to:
detect a cough of a user of the personal audio device based on the first and second signals,
wherein the first transducer is an external transducer and the second transducer is an in-ear transducer.

23. An apparatus for cough detection, comprising:
a first input for receiving a first signal from a first transducer of a personal audio device;
a second input for receiving a second signal from a second transducer of the personal audio device; and
one or more processors configured to:
detect a cough of a user of the personal audio device based on the first and second signals, wherein detecting the cough comprises:
determining a first energy in a first frequency band of the first signal;
determining a second energy in a second frequency band of the first signal; and
determining a third energy in a third frequency band of the second signal, wherein the first frequency band has a higher centre frequency than the second frequency band and the third frequency band.

* * * * *

UNITED STATES PATENT AND TRADEMARK OFFICE
CERTIFICATE OF CORRECTION

| | |
|---|---|
| PATENT NO. | : 11,653,855 B2 |
| APPLICATION NO. | : 17/541904 |
| DATED | : May 23, 2023 |
| INVENTOR(S) | : Lesso et al. |

It is certified that error appears in the above-identified patent and that said Letters Patent is hereby corrected as shown below:

In the Claims

1. In Column 14, Line 49, in Claim 5, delete "high pass" and insert -- high-pass --, therefor.

2. In Column 16, Line 3, in Claim 20, delete "method" and insert -- method comprising --, therefor.

Signed and Sealed this
Twenty-ninth Day of August, 2023

Katherine Kelly Vidal
*Director of the United States Patent and Trademark Office*